United States Patent [19]
Iga et al.

[11] Patent Number: 5,700,481
[45] Date of Patent: Dec. 23, 1997

[54] TRANSDERMAL DRUG DELIVERY PROCESS

[75] Inventors: Katsumi Iga, Suita; Shigeo Yanai, Himeji; Keiichiro Okabe, Komae; Masaki Itoh, Yokohama, all of Japan

[73] Assignees: Takeda Chemical Industries, Ltd., Osaka; Advance Co., Ltd.; Teikoku Hormone Mfg. Co., Ltd., both of Tokyo, all of Japan

[21] Appl. No.: 614,376

[22] Filed: Mar. 12, 1996

[30] Foreign Application Priority Data

Mar. 17, 1995 [JP] Japan ................................ 7-086290

[51] Int. Cl.⁶ ........................ A61F 13/00; A61N 1/30
[52] U.S. Cl. ........................ 424/449; 424/448; 604/20
[58] Field of Search ........................ 424/448, 449; 604/20

[56] References Cited

U.S. PATENT DOCUMENTS

| | | | |
|---|---|---|---|
| H1160 | 4/1993 | Maulding et al. | 604/20 |
| 5,250,022 | 10/1993 | Chien | 604/20 |

FOREIGN PATENT DOCUMENTS

| | | |
|---|---|---|
| 0 643 981 A1 | 3/1995 | European Pat. Off. . |
| 64-11564 | 1/1989 | Japan . |
| 64-11565 | 1/1989 | Japan . |
| 2-124176 | 5/1990 | Japan . |
| 91/08795 | 6/1991 | WIPO . |
| 91/15258 | 10/1991 | WIPO . |
| 92/04938 | 4/1992 | WIPO . |

*Primary Examiner*—D. Gabrielle Phelan
*Attorney, Agent, or Firm*—Wenderoth, Lind & Ponack

[57] ABSTRACT

A calcitonin, its derivative or a salt thereof is transdermally delivered by iontophoresis in which a substantially constant voltage in the range of 3 to 20 V is applied at an electric current of 0.05 to 0.5 mA/cm². In this process, the calcitonin can be delivered transdermally with a higher absorptivity by applying a higher voltage for a short period (at a voltage of about 6 to 14 V for about 5 to 15 minutes) in the initial stage of the voltage application, and then applying a lower voltage for a long period (at a voltage of about 3 to 9 V for about 30 to 40 minutes).

26 Claims, 5 Drawing Sheets

TRANSDERMAL DRUG DELIVERY PROCESS

BACKGROUND OF THE INVENTION

1. Field of the Invention

The present invention relates to a transdermal drug delivery process by iontophoresis which is useful for transdermal transmigration of a calcitonin to a living body (organism) with a high absorptivity.

2. Description of Related Art

Iontophoresis is a system for promoting transdermal absorption (endermic absorption) with the use of electricity. The principle of such iontophoresis basically resides in accelerating or enhancing transmittance of a drug molecule through a skin barrier by generating an electric field between an anode and a cathode to cause a positively charged molecule to move from the anode to the cathode, or to cause a negatively charged molecule to move from the cathode to the anode [see Journal of Controlled Release, 18, 213–220 (1992); Advanced Drug Delivery Review, 9, 119 (1992); Pharmaceutical Research, 3, 318–326 (1986)].

Recent advances of synthetic technologies and genetic engineering insure pure and mass production of a naturally-occurring peptide or protein, or a peptide or protein derivative in which the amino acid composition of the naturally-occurring peptide or protein is changed, or a chemically-modified derivative thereof. Further, such peptides and proteins are expected to be applied as drugs or medicaments. On the other hand, a strict control of administration (dosage) is required of these peptides or proteins each having a variety of physiological activities even in a small amount and for minimizing a side effect (adverse effect) for exhibition of the maximum drug effect in a specific disease. By way of illustration, a calcitonin has an activity of inhibiting (suppressing) decrease of the amount of a bone by means of inhibiting bone resorption, and hence is used for treatment (therapy) of osteoporosis, Paget's disease or other diseases. However, an excessive administration of the calcitonin causes a side effect such as anorexia (inappetence), and frequent administration (frequent dosage), that is, repeated administration with controlling an administration time is required for the therapy of the disease.

Further, a physiologically active peptide or protein is usually decomposed or degraded in a gastrointestinal tract (digestive tract) by a digestive fluid or juice and hydrolyzed by a hydrolase present in the digestive tract wall, and hence absorption efficiency of the peptide or protein can hardly be improved effectively. Therefore, for expecting a sufficient drug effect, such physiologically active peptide or protein is usually administered not orally but by an injection. Administration as an injectable preparation, however, causes a great pain and burden to a patient since such injectable preparation can not be administered by himself. In particular, when repeated administration over a long period is required such as in the calcitonin, the burden is increased.

In the field of pharmaceutical preparation, the iontophoresis method is intensively researched as a new drug delivery system. That is, use of iontophoresis provides an administration method for a drug by a patient himself, which has been formerly administered as an injectable preparation, and hence improves compliance and enhances the quality of life (QOL) of the patient.

With respect to a drug delivery process by iontophoresis, Japanese Patent Application Laid-open No. 11565/1989 (JP-A-64-11565) proposes a method of administering an ionic drug having a molecular weight of about 150 to 400 which comprises applying a voltage of 5 to 20 V to a skin for 1 to 60 seconds for decreasing the impedance of the skin as a pretreatment, and then applying a conductive voltage of 0 to 5 V to pass an electric current of 0.1 to 1 $mA/cm^2$. Japanese Patent Application Laid-open No. 11564/1989 (JP-A-64-11564) discloses a method which comprises applying a voltage of 5 to 20 V to a skin at a current density of not more than 1 $mA/cm^2$ for 1 to 60 seconds for decreasing the electric resistance of the skin, and applying a conductive voltage of 0 to 5 V to pass or apply an electricity at a current density of 0.1 to 1 $mA/cm^2$.

Japanese Patent Application Laid-open No. 124176/1990 (JP-A-2-124176) discloses a device for iontophoresis which is provided with a first output means for making an output of a direct-current voltage or a direct-current pulse and a second output means for making an output of a polarized pulse. This literature also discloses a transdermal administration of a liquid containing a drug by an application of the direct-current voltage (voltage 12 V or less, current density 0.3 $mA/cm^2$) or direct-current pulse and then applying a polarized pulse.

According to these iontophoresis technologies, however, sufficient transdermal absorption efficiency of a calcitonin can not be obtained.

SUMMARY OF THE INVENTION

It is, therefore, an object of the present invention to provide a process which insures an efficient transdermal delivery of a calcitonin with the use of the iontophoresis.

It is another object of the invention to provide a transdermal calcitonin delivery process which insures remarkable increase of the transdermal absorptivity and bioavailability of the calcitonin in a simple manner.

A further object of the invention is to provide an apparatus for iontophoresis and an electric applying method which are useful for enhancing the transdermal delivery of the calcitonin with the use of the iontophoresis.

The inventors of the present invention made intensive investigations to accomplish the above-mentioned objects, and found that an optimization of the electric applying condition of the iontophoresis results in marked increase (enhancement) of transdermal absorptivity of the calcitonin. The present invention has been accomplished based on the above findings and further investigations.

Thus, according to the transdermal drug delivery process of the invention, a calcitonin, its derivative or a salt thereof is transdermally transmitted by an iontophoresis in which a substantially constant direct-current voltage in the range of 3 to 20 V is applied at a current density of 0.05 to 0.5 $mA/cm^2$. In this process, the applied voltage may be decreased stepwise in a plural of time-series steps, with or without time interval. Further, applied voltages within a substantially same level may be applied in a plural of steps at time interval. As the direct-current voltage, either of a continuous direct-current voltage or a direct-current pulse voltage with a specific frequency may be used.

The apparatus of the present invention is provided with:

(1) an applicator comprising (1a) an electrode applicable with a direct-current voltage and (1b) an interface conductible to the electrode, capable of contacting a skin, possessing a calcitonin transmittablly and capable of being supplied with a liquid (solvent) for dissolving a calcitonin, (2) an electric power supply for application of a direct-current voltage to the electrode, and (3) a voltage stabilizing means for applying a substantially constant direct current voltage in the range of 3 to 20 V supplied from the electric power supply to the electrode with maintaining a current density at 0.05 to 0.5 mA/cm$^2$.

Further, the voltage applying method of the invention is a method of enhancing transdermal absorption of a calcitonin by iontophoresis with the use of the above applicator, which comprises applying a substantially constant voltage in the range of 3 to 20 V to the electrode with maintaining a current density (electric current) at 0.05 to 0.5 mA/cm$^2$.

It should be understood that the term "substantially constant voltage" as used in this specification means and includes not only an applied voltage always in a constant level but also an applied voltage in which an applied voltage value varies within a fluctuation range of ±20%.

DETAILED DESCRIPTION OF THE INVENTION

Figure 1:
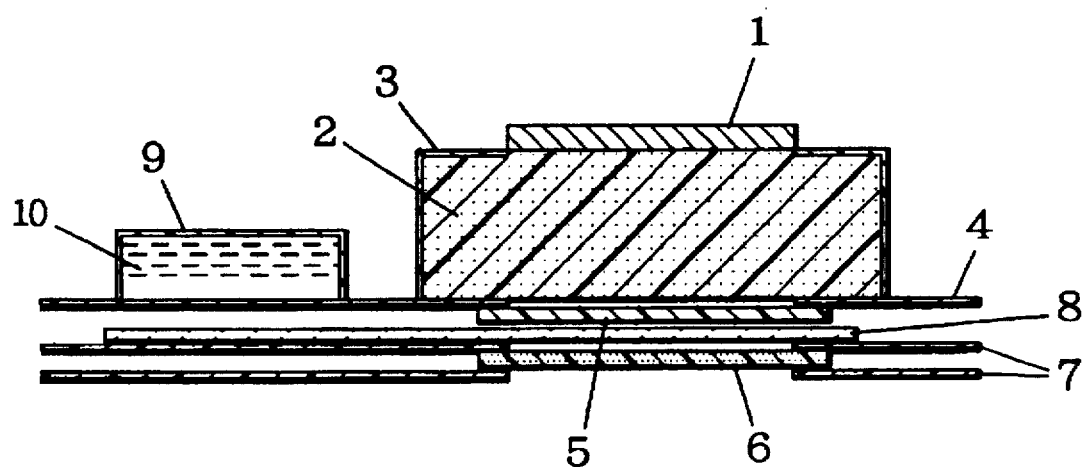
FIG. 1 is a cross sectional view illustrating an applicator A used in Example 1.

In the transdermal delivery process by iontophoresis of the present invention, a substantially constant voltage selected from the range of about 3 to 20 V, preferably about 4 to 15 V and more preferably about 5 to 14 V is applied to a skin. The applied current density (electric current) may be about 0.05 to 0.5 mA/cm$^2$ (e.g. about 0.05 to 0.45 mA/cm$^2$), preferably about 0.08 to 0.5 mA/cm$^2$, and more preferably about 0.08 to 0.3 mA/cm$^2$ (e.g. about 0.08 to 0.28 mA/cm$^2$). For the purpose of suppressing or restraining a local current of electricity, a current density of 0.1 to 0.3 mA/cm$^2$ may practically be employed.

According to the process of the invention, the voltage application may be effected by applying a voltage, suitably selected from the above-mentioned voltage and current density ranges, to a skin continuously or intermittently at time interval. By way of an example, when an electricity is applied or passed in a plural of steps at time interval (i.e. in a case of applying a voltage a plural of times transmittently), the applying period and applying interval (a period of interrupting the voltage-application) are not specifically restricted as far as not interfering with the efficiency of the transdermal delivery, and for example, the applying period per applying step is about 1 to 60 minutes, preferably about 2 to 45 minutes (e.g. about 5 to 30 minutes), and more preferably about 3 to 30 minutes (e.g. about 10 to 30 minutes). The voltage application interval may liberally be selected from the range of about 1 second to 60 minutes, and for instance is about 30 seconds to 30 minutes (e.g. about 1 to 30 minutes) and practically about 1 to 10 minutes.

Further, the electric passing (voltage application) may be carried out in a plural of steps in which the applied voltages varies or differs stepwise in the above-specified voltage range of 3 to 20 V. Preferably, a voltage may be applied with time-series decrease of the applied voltage (potential) continuously or stepwise within the above-specified range of 3 to 20 V. In particular, when a plural of voltage application steps are employed, the voltage in a following (succeeding) voltage application step may preferably be decreased continuously or stepwise in comparison with the precedent voltage application step. The succeeding voltage application step may be conducted continuously (without interruption or time interval), or may be effected at time interval, respectively relative to the precedent voltage application step. The use of such voltage application method has such advantages as to maintain a high transdermal (percutaneous) transmittance of the calcitonin with mitigating or relieving a skin irritation and hence to enhance or accelerate the transdermal absorption of the calcitonin. Incidentally, although it is important in iontophoresis to increase the transmissibility (permeability) of the calcitonin in condition for a minimized or mitigated stimulus or irritation of a subject, a skin irritation is increased with an increasing voltage which is applied in order to improve the transdermal absorption of the calcitonin. On the other hand, when the applied voltage is reduced or the voltage application period is shortened, the skin transmissibility (skin transmissibility) of the calcitonin can not sufficiently be enhanced, although the skin irritation may be mitigated.

In more concretely, when a voltage application cycle comprising two voltage application (electric passing) steps is employed, a combination use of a first voltage application step of applying a higher constant voltage among the above-specified voltage range for a short time, and, after the first voltage application step, a second voltage application step of applying a lower constant voltage than that of the first voltage application step for a long period results in maintenance or keeping of the skin transmissibility of the calcitonin even when the voltage of the successive second voltage application step is low, and hence the calcitonin can effectively be delivered or transmitted via skin (transdermally) with a high efficiency. Especially, when the voltage application period of the first voltage application step is shortened, the skin irritation can be mitigated or relieved even when a higher constant voltage within the above-specified voltage range is applied.

The first voltage application step (precedent electric passing step) may be effected, for example, by applying a constant voltage (potential difference) selected from the range of about 4 to 15 V (e.g. about 5 to 15 V) and preferably about 6 to 14 V, for about 1 to 30 minutes, preferably about 5 to 20 minutes and more preferably about 5 to 15 minutes. The voltage in the first voltage application step may practically be not higher than 12 V (volt). The second voltage application step (following electric passing step) may be carried out at a constant voltage selected from the range of about 1 to 10 V and preferably about 3 to 9 V, with a voltage application period of about 15 to 100 minutes, preferably about 20 to 60 minutes and more preferably about 30 to 40 minutes.

When the applied voltage is stepwise decreased or lessened in a plural of the voltage application steps at time intervals, the voltage application interval (passing-interrupting period) may be selected from the above-mentioned range.

Further, an application of a substantially same voltage with maintaining the above current density in a plural of voltage application steps at time interval also insures mitigation of the skin irritation advantageously. In particular, for the purpose of enhancing (promoting) the transdermal absorption of the calcitonin with mitigating or alleviating the skin irritation (irritation to a skin), the process of the invention includes a process for accelerating the transdermal absorption (endermic absorption) of the calcitonin which comprises at least one cycle comprising (i) a voltage application step of applying a substantially constant voltage in the range of 4 to 15 V for 1 to 30 minutes, (ii) a step of stopping or interrupting the voltage application for 1 to 30 minutes, and the above-mentioned voltage application step (i).

More preferred process includes a process which comprises at least one cycle comprising (a) a voltage application step of applying a substantially constant voltage in the range of 6 to 14 V for 1 to 30 minutes with maintaining a current density of 0.1 to 0.3 mA/cm$^2$, (b) a step of interrupting the voltage application for 1 to 30 minutes and the above voltage application step (a).

The voltage application cycle comprising plural voltage application steps may be repeated not only once but also plural times. When a plural of the voltage application cycles are applied after the first (initial) voltage application cycle, the applied voltages and the voltage application periods in the succeeding plural voltage application cycles may be different with each other.

The electric power supply (power source) for the iontophoresis is not strictly restricted as far as generating a direct-current voltage (potential), and may only generate either of a continuous direct-current voltage or a direct-current pulse voltage, and be applicable to a skin. Preferable direct-current voltage includes, for instance, a direct-current pulse voltage. The direct-current pulse voltage may be a symmetrical wave, an asymmetrical wave, a sow-tooth wave (pulse) or a triangular pulse (chopping wave) but preferred is a square direct-current pulse voltage.

The frequency of the direct-current pulse voltage may be selected from a broad range and is liberally selected from the range of, for example, about 0.1 to 200 kHz, preferably about 1 to 100 kHz (e.g. about 10 to 100 kHz), and more preferably about 5 to 80 kHz (e.g. about 10 to 50 kHz). The frequency of the direct-current pulse may practically be about 1 to 60 kHz (e.g. about 10 to 60 kHz), and preferably about 1 to 50 kHz (e.g. about 30 to 40 kHz).

The proportion of the time (period) of applying the voltage per cycle in the direct-current pulse voltage (duty % or duty ratio) is not particularly limited, and is suitably selected from the range of, for example, about 10 to 90%, preferably about 10 to 70% and more preferably about 20 to 40%. The ratio of period of applying the voltage per cycle in the direct-current pulse voltage (i.e. the period when the electric passing is ON) may practically be about 30 to 50%.

Further, the contact area (touch area) of the interface (contactor or patch) which comprises a matrix possessing (holding) the calcitonin with a skin is not critical and can be selected from a broad range, for instance, of about 0.5 to 100 cm$^2$, preferably about 1 to 50 cm$^2$ and practically about 2 to 25 cm$^2$ (e.g. about 2 to 20 cm$^2$).

The total voltage application period (term) can be selected according to the conditions of the voltage application, dose or other factors, and is for example about 24 hours or shorter, preferably about 12 hours or shorter (e.g. about 10 minutes to 7 hours) and more preferably 6 hours or shorter (e.g. about 20 minutes to 3 hours), for a continuous voltage application. The voltage application period (electric passing period) may practically be about 30 minutes to 2 hours.

According to the present invention, a calcitonin, its derivative or a salt thereof can effectively be transdermally delivered (administered) to a subject or patient. The calcitonin may be whichever of calcitonins derived from mammals (for example, a human being or a swine), birds (e.g. chicken), fishes (e.g. a salmon, an eel, etc.) or other animals or plants (vegetables). The calcitonin may also be a chimera of, for instance, a human and a salmon. Further, whichever of a naturally-occurring calcitonin or a chemically synthesized calcitonin can be employed. Moreover, the calcitonin may also be a calcitonin in which a part or the whole of the structure of the amino acids constituting the calcitonin or the structure of the side chain is artificially changed or modified.

Typical example of the calcitonin includes a peptide shown by the following formula (I) [Endocrinology, 1992, 131/6 (2885–2890):

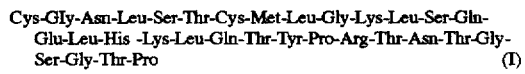

Cys-Gly-Asn-Leu-Ser-Thr-Cys-Met-Leu-Gly-Lys-Leu-Ser-Gln-
Glu-Leu-His -Lys-Leu-Gln-Thr-Tyr-Pro-Arg-Thr-Asn-Thr-Gly-
Ser-Gly-Thr-Pro  (I)

Further, as a derivative having a similar function or activity to the calcitonin, there may be mentioned, for instance, a compound shown by the following formula (II) or its salt [Endocrinology, 1992 131/6 (2885–2890)]:

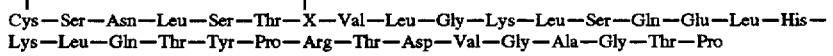

(II)
Cys—Ser—Asn—Leu—Ser—Thr—X—Val—Leu—Gly—Lys—Leu—Ser—Gln—Glu—Leu—His—
Lys—Leu—Gln—Thr—Tyr—Pro—Arg—Thr—Asp—Val—Gly—Ala—Gly—Thr—Pro wherein X represents 2-aminosberic acid.

Examples of the salt of the calcitonin include salts with inorganic acids such as hydrochloric acid, sulfuric acid, hydrobromic acid and phosphoric acid; salts with organic acids such as formic acid, acetic acid, propionic acid, glycolic acid, oxalic acid, succinic acid, tartaric acid, citric acid, benzenesulfonic acid and p-toluenesulfonic acid; complex salts with inorganic compounds such as calcium, magnesium and so on.

For the delivery (administration or dosage) of the calcitonin, a variety of applicators (adapters) can be employed. Such applicator may be composed of, for instance, an electrode applicable with a direct-current voltage, an interface which is conductible to the electrode, capable of contacting a skin, and possesses or holds the calcitonin transmittablly or permeably, and a supply means for supplying or feeding a solvent for the calcitonin to the interface.

An applicator illustrated in FIG. 1 is provided with a support (base member) 4 having a flexibility and being formed with an opening, and an electrode 1 such as a silver electrode. Further, the applicator is provided with a first container (reservoir) 3 and a second container (reservoir) 9, and the first container 3 accommodates an electrically conductive gel 2 such as a hydrated gel of NaCl-containing poly(vinyl alcohol) (PVA), and is disposed in the part corresponding to the opening on the support 4, and the second container 9 reserves a liquid (fluid) 10 for dissolution of the calcitonin, such as a distilled water for injection (Fuso Chemical Industries, Ltd., Japan), and constitutes a reservoir disposed on the support 4.

The opening of the support 4 which is formed for insuring the movement of electric charges is provided with an ion exchange membrane 5, the inner surface of which faces to the electrically conductive gel 2 of the container 3, and the outer surface of the ion exchange membrane is laminated with a porous body (matrix) 6 having a porous or capillary structure, through a nonwoven fabric 8a disposed in the area from the opening of the support 4 (the part of the container 3) toward the part of the second container 9. Meanwhile, the porous body (matrix) 6 and the calcitonin possessed in the porous body constitute an interface (patch) capable of contacting with a skin. To the porous body 6 is attached an adhesive tape 7 for applying the applicator to a skin with the part of the porous body 6 corresponding to the opening of the support 4 being contactible with a skin. The electrically conductive gel 2 of the first container 3 is conductible with the electrode 1 and capable of contacting the ion exchange membrane 5 through the opening. The size of the opening of the support 4 is not particularly limited, but the area of the opening may preferably be almost the same size with the area of the surface to be contacted by a skin (skin contact area) of the interface (porous body)

The containers 3, 9 can be formed of, for instance, polyethylene or other synthetic resins. As the ion exchange membrane 5, use can be made of various membranes each having ion exchange capability, such as "AC220 Membrane" (trade name) manufactured by Asahi Chemical Industries, Japan. As the nonwoven fabric 8a, a variety of nonwoven fabrics through which a liquid is permeable or transmittable, such as "Benberg Half" (trade name) manufactured by Asahi Chemical Industries, Japan may be used. Further, various organic porous bodies or inorganic porous bodies which can possess the calcitonin by adsorption, supporting or other technology, such as porous membrane of a nylon porous body (trade name: "Biodyne Plus", Nihon Pall Ltd., Japan) and the like can be used as the porous body 6. As the adhesive tape 7, various adhesive tapes each having adhesive property (tackiness) to a skin, such as "Blenderm" (trade name) manufactured by 3M Pharmaceuticals, M. N. (Minnesota) may be employed.

Such applicator may be pierced by, for example, inserting a needle therough the second container 9 and the support 4 to form a pore in the support 4 connecting to the inside of the second container 9, so that the liquid 10 for dissolution of the calcitonin is permeated through the nonwoven fabric 8a to reach (to be supplied or fed) to the porous body 6 possessing the calcitonin.

Incidentally, the second container is not always necessary, and a liquid for dissolving the calcitonin may be injectable (feedable) to the interface retaining the calcitonin. In such an embodiment of an applicator, the nonwoven fabric is not necessarily required.

Figure 2:
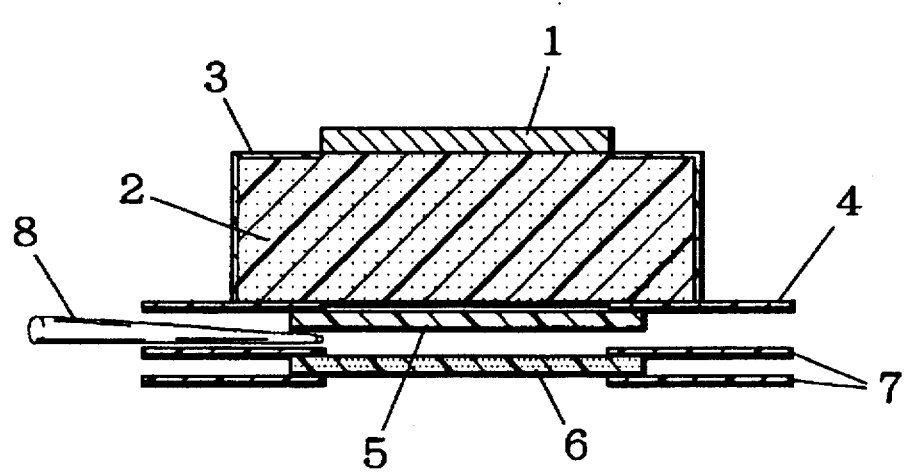
FIG. 2 is a cross sectional view of an applicator B used in Example 2.

FIG. 2 is a cross sectional view illustrating another embodiment of an applicator. This applicator is provided with a support, and a first container 3 having an electrode 1 and accommodating an electrically conductive gel 2 in the same manner with the applicator shown in FIG. 1. Further, a porous body 6 is laminated (piled up), through an ion exchange membrane 5, on the part corresponding to an opening of the support 4. Furthermore, an adhesive tape (pressure-sensitive tape) 7 is attached to the porous body 6 with remaining the part of the porous body 6 corresponding to the opening of the support 4 capable of contacting a skin, in the same manner as above. Between the ion exchange membrane 5 and the interface 6 is formed an injection port which is injectable with a liquid.

When such applicator is used, a nozzle tip of a injection tip 8b may be inserted to the injection port between the ion exchange membrane 5 and the porous body 6 to inject a liquid for dissolving the drug such as a distilled water for injection to the porous body 6 possesing or retaining the calcitonin. The injecting amount of the liquid may be selected from a range, according to the size of the applicator, the surface area of the porous body, the retaining amount (retention capacity) of the drug (calcitonin), as far as the calcitonin can be dissolved, and usually is about 30 to 500 µl and preferably about 50 to 200 µl.

For the purpose of minimizing or suppressing the loss of the calcitonin due to the porous body, use may preferably be made of a porous body which has been subjected to a pretreatment with a suitable adsorption-inhibitor (e.g. a serum albumin, benzalkonium chloride, etc.). Further, it is also effective to incorporate an absorption accelerator (e.g. monoterpenes, fatty acid monoglycerides, etc.) for accelerating the absorption of the calcitonin into the liquid for dissolution of the drug (calcitonin).

The transdermal calcitonin delivery (administration) by means of iontophoresis can be effected by applying a direct-current voltage to the electrode of the applicator and a reference electrode each adhered to a skin for applying an electricity in such a manner as the electrode of the applicator being an anode and the reference electrode provided with, for example, a silver chloride electrode being a cathode. That is, by allowing the skin contact surface of the interface constituting the applicator and the reference electrode and applying a voltage, a current circuit can be formed as the skin being an electric conductor so that the transdermal drug delivery by iontophoresis can be effected. Incidentally, when a voltage is applied, the electrode and the reference electrode may be disposed adjacently, but preferably be disposed in the distant (or opposite) parts on the skin. The materials of the electrode and the reference electrode are not strictly limited, and these electrode may be formed by, for instance, silver and other metals, electric conductive rubbers, electric conductive polymers, aluminum foils and other metal foils.

The use of such applicator insures transdermal calcitonin delivery without causing a pain to a patient, and provides a self-administration. Further, according to the voltage application in the above condition with the use of the applicator, the transdermal absorption of the calcitonin by iontophoresis can significantly be accelerated or enhanced.

The apparatus of the present invention is provided with the above-mentioned applicator, an electric power supply and a voltage stabilizing means. That is, the apparatus of the invention for enhancing the transdermal absorption of the calcitonin with utilizing iontophoresis is provided with the applicator, the electric power supply (electric source) for applying a direct-current voltage to the electrode of the applicator, and the voltage stabilizing means for applying a substantially constant direct-current voltage in the range of 3 to 20 V supplied from the electric power supply to the electrode with maintaining a current density (electric current) at 0.05 to 0.5 mA/cm$^2$. As the voltage stabilizing means, a variety of means (voltage stabilizer) such as Zener diode or other constant voltage element, a stabilizing circuit with the use of a feedback loop and other means may be employed. The stabilizing circuit may be composed of, for example, a reference voltage part for establishing or settling a reference voltage with using Zener diode or other means, a detector part for detecting an applied voltage, a compare part for comparing the detected value detected in the detector part with a reference (basis) in the reference voltage part, and a control part for stabilizing an output voltage responding to the compared result in the compare part.

Further, in the apparatus of the invention, the delivery (administration) of the calcitonin by iontophoresis can be controlled or regulated by programming delivery period per day and the one cycle of the voltage application step to a control unit (control device) in relation with the applicator. The calcitonin may also be automatically delivered via skin by programming the applied voltage, voltage application period and voltage application interval (interrupting period) to the control device in relation with the contact area of the interface, dose of the calcitonin or other factors.

Such apparatus and voltage application method provides transdermal delivery of even the calcitonin, which requires repeated administration over a long period, with a high efficiency in a simple and easy manner, so that they are useful for therapy (treatment) for various diseases where plasma calcium level requires to be reduced, such as osteoporosis and Paget's disease (osteitis deformans). Incidentally, the apparatus and the processes of the present invention can be applied not only human beings but also dogs, cats, horses, cows, rabbits, swine and other mammals.

According to the present invention, the calcitonin can be absorbed transdermally with a high efficiency since a voltage application is conducted in the specific condition with the use of iontophoresis. Further, the transdermal absorptivity of the calcitonin can remarkably be enhanced and the bioavailability thereof can be improved in such a simple and easy manner as controlling the applied voltage and the electric density.

The following examples are intended to illustrate the invention in more detail, but should by no means limit the scope of the invention.

EXAMPLES

Example 1

An abdominal skin of a SD rat (male, 7-week aged) was clipped with a hair clipper and treated with a shaver under pentobarbital-anesthetization, and was slightly rubbed with an absorbent cotton (cotton wool) containing a 70% aqueous solution of ethanol for defatting and disinfection. By using the Applicator A shown in FIG. 1 or the Applicator B illustrated in FIG. 2, a skin contact surface of the drug-possessing membrane (Biodyne Plus), which had been pretreated with 10% bovine serum albumin (BSA) and possessed 20 µg (as a dry matter) of a salmon calcitonin (Teikoku Hormone Mfg. Co., Ltd.) per one membrane was attached and fixed to the abdominal skin of the rat. Meanwhile, in the Applicator A shown in FIG. 1, the dried drug was dissolved immediately before use by supplying or feeding water to the membrane from the reservoir. In the applicator B illustrated in FIG. 2, the applicator was first attached or adhered to the skin and then the dried drug was dissolved by supplying 120 µl of a distilled water from an injection tip. Further, a silver chloride electrode (2.5 cm²) as a reference electrode was adhered and fixed in the opposite part to the adhered part of the applicator via an electrically conductible gel comprising 10% PVA gel containing 0.9% of NaCl in a thickness of 2 mm.

Then, a continuous voltage application for 15 minutes was repeated for 3 times at a time interval of 5 minutes in the following manner. That is, the voltage application was effected by a direct-current pulse application (depolarizing constant voltage square pulse application) with a frequency of 40 kHz and a duty (pulse-duty factor) of 30% using the applicator as an anode and the reference electrode as a cathode, with changing the applied voltage as follows. In the respective voltage application, observed electric current in the initial stage of the voltage application was respectively determined for each rat. The current density as a mean value for the subjects are as follows.

(1) Applicator A: voltage 6 V current density about 0.04 mA/cm²

(2) Applicator B: voltage 12 V current density about 0.24 mA/cm²

(3) Applicator C: voltage 12 V current density about 0.24 mA/cm²

Blood was took from jugular veins (cervical vein) of the rat and centrifuged at a rate of 12,000 rpm for 10 minutes, and the concentration of the salmon calcitonin in the obtained serum sample was determined by a radioimmunoassay method. The results are illustrated in FIG. 3.

Figure 3:
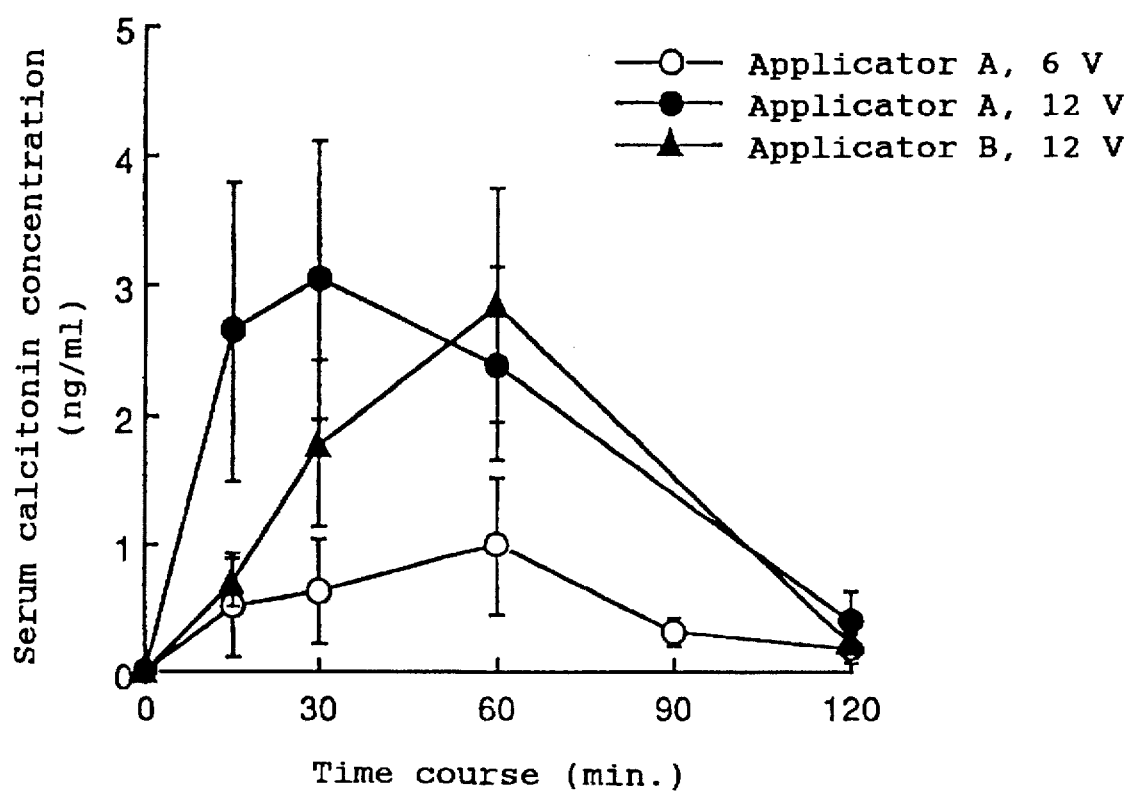
FIG. 3 is a graph showing the results obtained in Example 1.

As shown in FIG. 3, according to the iontophoresis (2) and (3) in which the applied voltage was 12 V, the salmon calcitonin concentration in the serum can be increased in comparison with the iontophoresis (1) in which the applied voltage was 6 V. Further, the bioavailability (BA) was evaluated from the ratio of the area under the serum salmon calcitonin concentration-time curve (AUC value) of the tested group relative to the AUC value obtained by intravenous administration on the same dose basis [actual intravenous dose, 0.3 µg of calcitonin]. As a result, the bioavailabilities of the calcitonin were 4.6% (Applicator A) for the applied voltage of 6 V, and 16.6% (Applicator A) and 16.6% (Applicator B), respectively for the applied voltage of 12 V. Thus, an application of a voltage of 12 V enhances the bioavailability in comparison with the applied voltage of 6 V.

Example 2

Under pentobarbital-anesthetization, an abdominal skin of a SD rat (male, 7-week aged) was clipped with a hair clipper and treated with a shaver, and was slightly rubbed with an absorbent cotton (cotton wool) containing a 70% aqueous solution of ethanol for defatting and disinfection. With the use of the Applicator B illustrated in FIG. 2, a surface or side for contacting a skin of a drug-retaining membrane (1) or a drug-retaining membrane (2) was adhered and fixed to the abdominal skin of the rat. The drug-retaining membranes (1) and (2) had been pretreated with 0.01% benzalkonium chloride (BAC) and possessed 10 µg (on the dried basis) of the salmon calcitonin and 20 µg (on the dried basis) of the salmon calcitonin, respectively. Further, a reference electrode was applied and fixed to the skin in the same manner as Example 1. Then, the dried drug was dissolved by supplying 120 µl of distilled water from an injection tip. A pulse voltage application at a direct-current voltage of 12 V with a frequency of 40 kHz and a duty of 30% for 15 minutes was repeated for 3 times at a time interval of 5 minutes. The current density determined in the initial stage of the voltage application was about 0.24 mA/cm² as a mean value of the each rat. Thus, the salmon calcitonin concentration in the serum was evaluated in the same manner as Example 1, and the results are shown in FIG. 4.

Figure 4:
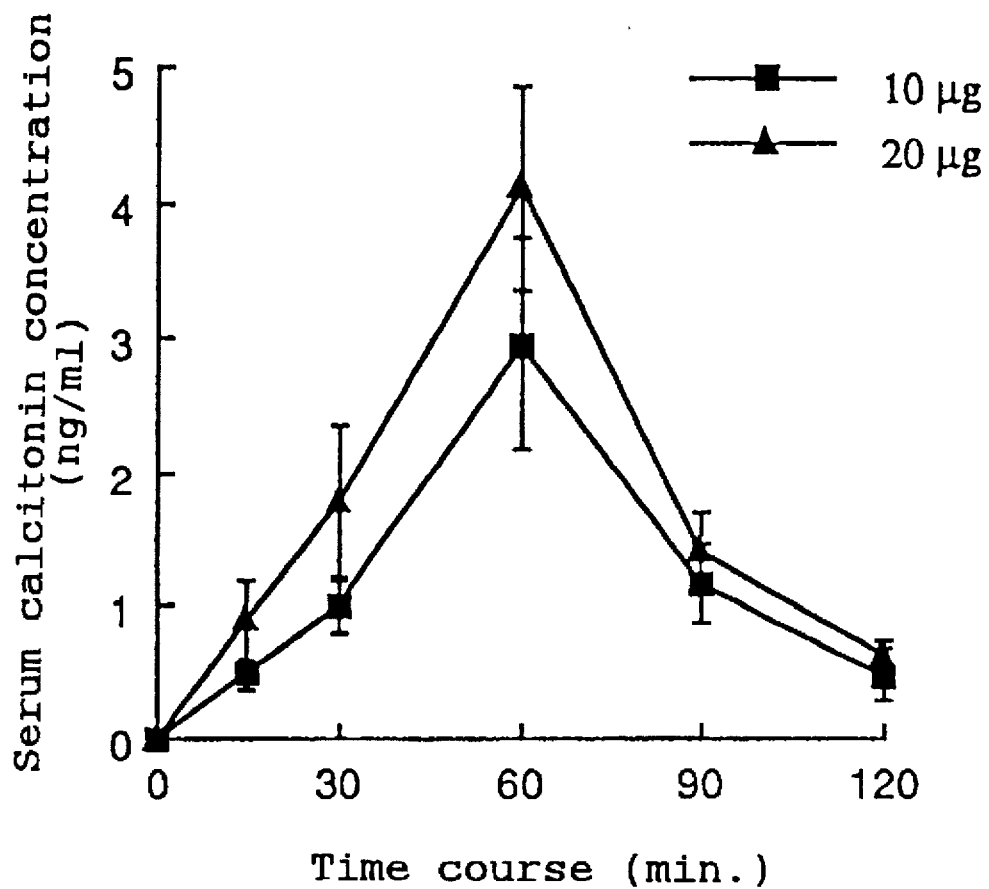
FIG. 4 is a graph illustrating the results obtained in Example 2.

As shown in FIG. 4, the serum salmon calcitonin concentration could be controlled according to the possessing amount (retention capacity) of the salmon calcitonin in the iontophoresis in which a voltage of 12 V was applied. The bioavailabilities (BA) were such high values of 23.3% for the calcitonin possessing amount of 10 µg in the drug-retaining membrane (1), and 16.6% for the calcitonin possessing amount of 20 µg in the drug-retaining membrane (2).

Example 3

Figure 5:
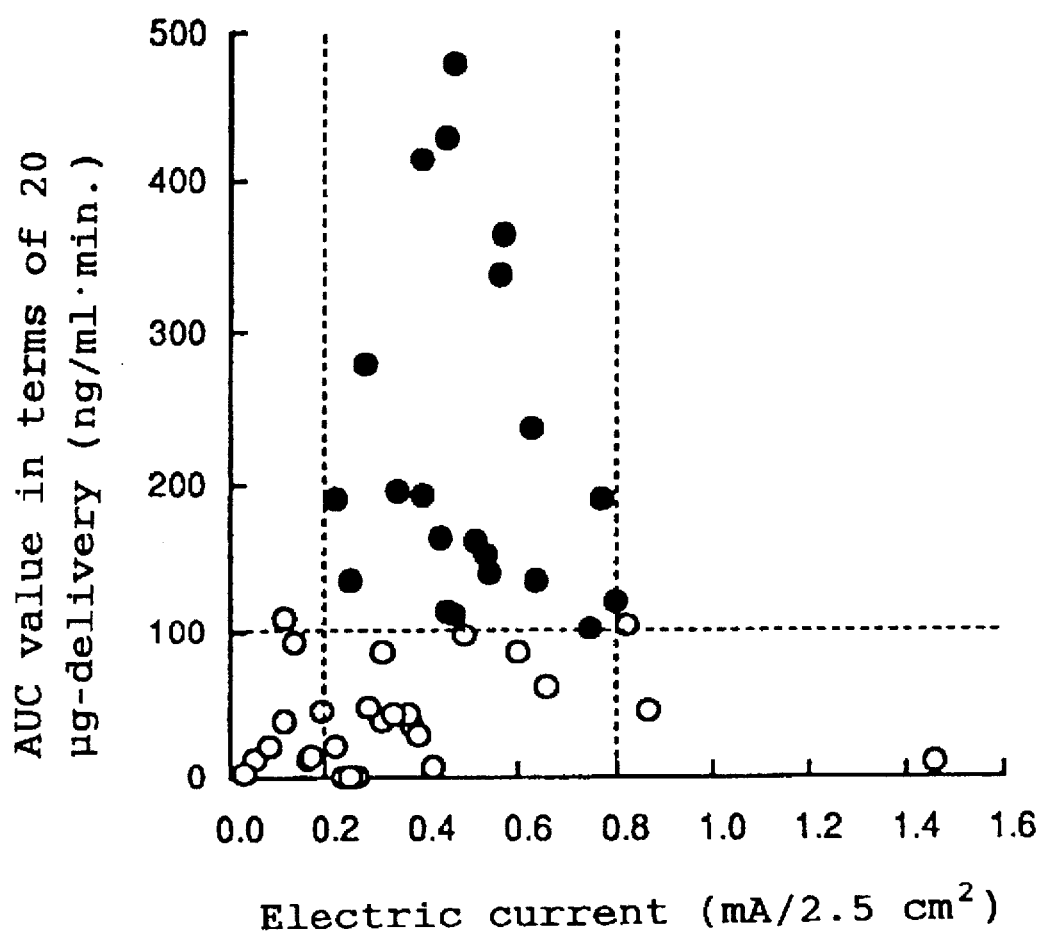
FIG. 5 is a graph indicating the results obtained in Example 3.

The correlation between the electric current value in the initial stage (1 minute) of the administration and the AUC value in terms of the dosage of 20 µg was evaluated based on the test results obtained by repeating the procedures of Example 1 and Example 2 for the total of 48 times. The results are set forth in FIG. 5. As apparent from FIG. 5, large AUC values could be obtained in the current value of the initial of the administration within the range of 0.2 mA/2.5 cm$^2$ to 0.7 mA/2.5 cm$^2$ (0.08 to 0.28 mA/cm$^2$).

Example 4

An abdominal skin of a male SD rat (7-week aged) was clipped with a hair clipper and treated with a shaver under pentobarbital-anesthetization, and was slightly rubbed with an absorbent cotton holding a 70% aqueous solution of ethanol for defatting and disinfection. By using the Applicator A illustrated in FIG. 1, a surface to be contacted by a skin of a drug-possessing membrane pretreated with 0.01% benzalkonium chloride (BAC) and possessing 4 µg (on the dried basis) of the salmon calcitonin per membrane was applied and fixed to the abdominal skin of the rat. Immediately before the use of the applicator, the dried drug was dissolved by supplying water from the reservoir. Further, a reference electrode was attached and fixed to the skin in the same manner as Example 1.

Then, in the common condition of a frequency of 30 kHz and a duty of 50%, the calcitonin was transdermally delivered according to the following processes:

(1) a process of applying a voltage of 12 V for 5 minutes and, without interruption, applying a voltage of 7.5 V for 40 minutes, (2) a process of applying a voltage of 12 V for 15 minutes and, without interruption, applying a voltage of 7.5 V for 30 minutes, and (3) a process of applying a voltage of 12 V for 15 minutes.

Figure 6:
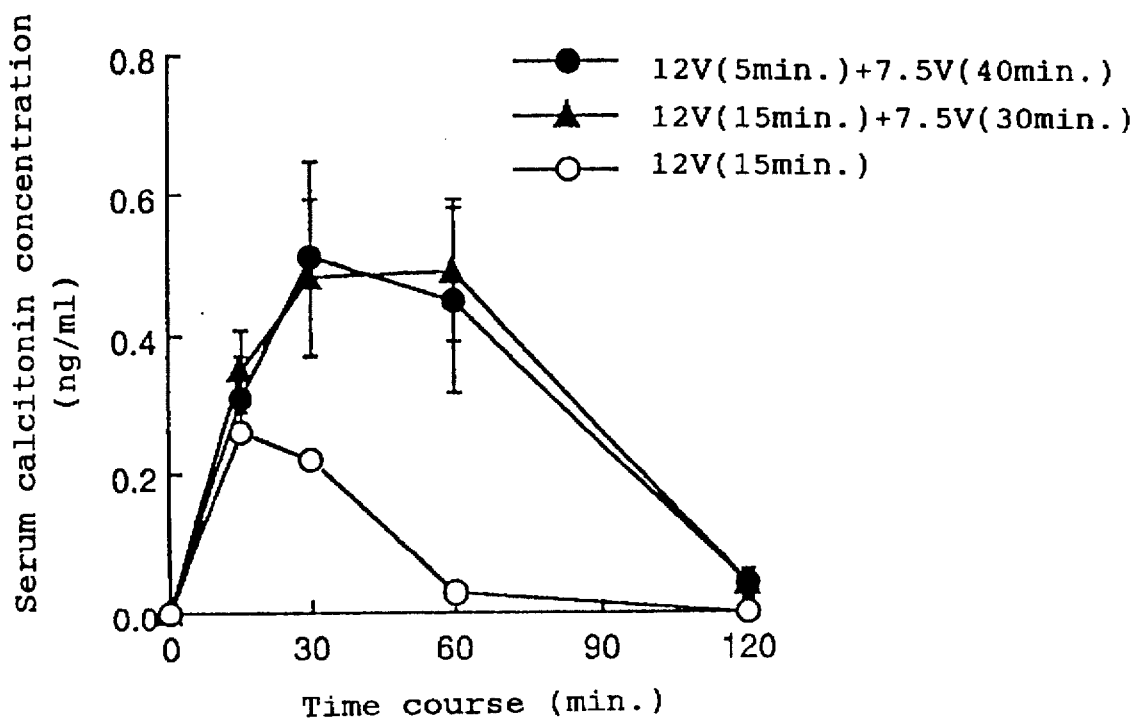
FIG. 6 is a graph illustrating the results obtained in Example 4.

The salmon calcitonin concentrations in the serum were evaluated in the same manner as Example 1, and the results are illustrated in FIG. 6.

As illustrated in FIG. 6, when a high voltage was applied in the initial stage of the voltage application as in the processes (1) and (2), the serum salmon calcitonin concentration was high even when the voltage application at a lower voltage was followed, compared with the process (3) in which voltage application was conducted at a voltage of 12 V for 15 minutes. The bioavailabilities (BA) each obtained in the processes (1), (2) and (3) were 13.6%, 14.2% and 3.6%, respectively. Thus, a high bioavailability was obtained by applying a lower voltage following an application of a higher voltage in the initial stage of the voltage application for a short period.

What is claimed is:

1. A transdermal drug delivery process by iontophoresis for a calcitonin, its derivative having similar function or activity to the calcitonin or a salt thereof, which comprises the step of applying a substantially constant voltage within the range of 3 to 20 V at a current density of 0.05 to 0.5 mA/cm$^2$, wherein the process comprises:

(1) at least one cycle comprising:
(1a) a precedent voltage application step of applying a substantially constant voltage for 1 to 30 minutes, and
(1b) a succeeding voltage application step of applying a substantially constant voltage, which voltage is lower than the applied voltage of the precedent voltage application step (1a), for 15 to 100 minutes, or (2) at least one cycle comprising;
(2a) a voltage application step of applying a substantially constant voltage in the range of 4 to 15 V for 1 to 30 minutes.
(2b) a step of interrupting the voltage application for 1 to 30 minutes, and
(2c) a voltage application step of applying a substantially constant voltage, which voltage is substantially the same as the applied voltage of the voltage application step (2a) and in the range of 4 to 15 V, for 1 to 30 minutes.

where the current density in the voltage application steps (2a) and (2c) is maintained at 0.08 to 0.3 mA/cm$^2$.

2. A transdermal drug delivery process according to claim 1, wherein the voltage in the voltage application steps (1a) and (1b) is 4 to 15 V.

3. A transdermal drug delivery process according to claim 1, wherein the current density in the voltage application steps (1a) and (1b) is 0.08 to 0.5 mA/cm$^2$.

4. A transdermal drug delivery process according to claim 1, wherein the current density in the voltage application steps (1a) and (1b) is 0.08 to 0.3 mA/cm$^2$.

5. A transdermal drug delivery process according to claim 1, wherein a substantially constant voltage within the range of 4 to 15 V is applied at a current density of 0.08 to 0.3 mA/cm$^2$ in the voltage application steps (1a) and (1b).

6. A transdermal drug delivery process according to claim 1, wherein the process comprises the steps of:
(1a) a precedent voltage application step of applying a substantially constant voltage in the range of 5 to 15 V for 1 to 30 minutes, and
(1b) a succeeding voltage application step of applying a substantially constant voltage, which voltage is lower than the applied voltage of the precedent voltage application step and in the range of 1 to 10 V, for 15 to 100 minutes.

7. A transdermal drug delivery process according to claim 1, wherein the applied voltage of the precedent voltage application step (1a) is 6 to 14 V.

8. A transdermal drug delivery process according to claim 1, wherein the voltage application period of the precedent voltage application step (1a) is 5 to 20 minutes.

9. A transdermal drug delivery process according to claim 1, wherein the applied voltage of the succeeding voltage application step (1b) is 3 to 9 V.

10. A transdermal drug delivery process according to claim 1, wherein the voltage application period of the succeeding voltage application step (1b) is 20 to 60 minutes.

11. A transdermal drug delivery process according to claim 1, wherein the process comprises the steps of;
(1a) a precedent voltage application step of applying a substantially constant voltage in the range of 6 to 14 V for 5 to 15 minutes, and
(1b) a succeeding voltage application step of applying a substantially constant voltage, which voltage is lower than the applied voltage of the precedent voltage application step (1a) and in the range of 3 to 9 V, for 30 to 40 minutes.

12. A transdermal drug delivery process according to claim 1, wherein a direct-current pulse voltage with a frequency of 0.1 to 200 kHz is applied.

13. A transdermal drug delivery process according to claim 1, wherein a direct-current pulse voltage with a frequency of 1 to 100 kHz is applied.

14. A transdermal drug delivery process according to claim 12, wherein the ratio of the voltage application period per cycle in the direct-current pulse voltage is 10 to 90%.

15. A transdermal drug delivery process according to claim 1, wherein a substantially constant voltage in the range of 4 to 15 V is applied at a current density of 0.08 to 0.3 mA/cm$^2$ with the use of a direct-current pulse voltage having a frequency of 1 to 100 kHz and a ratio of a voltage applying period per cycle of 10 to 70%.

16. A transdermal drug delivery process according to claim 1, wherein a substantially constant voltage in the range of 6 to 14 V is applied for 5 to 15 minutes in the precedent voltage application step (1a), and subsequently a substantially constant voltage in the range of 3 to 9 V is applied for 30 to 40 minutes in the succeeding voltage application step (1b), with the use of a direct-current pulse voltage having a frequency of 1 to 100 kHz and a ratio of voltage application period per cycle of 10 to 70% and with maintaining a current density at 0.08 to 0.3 mA/cm$^2$.

17. A transdermal drug delivery process according to claim 1, wherein a substantially constant voltage in the range of 6 to 14 V is applied for 5 to 15 minutes in the precedent voltage application step (1a), and then a substantially constant voltage in the range of 3 to 9 V is applied for 30 to 40 minutes in the succeeding voltage application step (1b), with a proviso that a direct-current pulse voltage having a frequency of 1 to 50 kHz and a ratio of a voltage applying period per cycle of 10 to 70% is used and the skin contact area of the iontophoresis is 1 to 50 cm$^2$.

18. A transdermal drug delivery process according to claim 1, wherein wherein the process comprises (1) the steps of;

(1a) the precedent voltage application step, (1c) a step of interrupting the voltage application for 1 to 30 minutes, and (1b) the succeeding voltage application step.

19. A transdermal drug delivery process according to claim 1, wherein the process comprises (2) at least one cycle comprising;

(2a) a voltage application step of applying a substantially constant voltages in the range of 6 to 14 V for 1 to 30 minutes, where the voltage is a direct-current pulse voltage with a frequency of 1 to 50 kHz having a ratio of a voltage applying period per cycle of 10 to 70%, and the area to be contacted by a skin in the iontophoresis is 1 to 50 cm$^2$ and the current density is maintained at 0.1 to 0.3 mA/cm$^2$, (2b) a step of interrupting the voltage application for 1 to 30 minutes, and (2c) a voltage application step of applying a substantially constant voltage, which voltage is the same as the applied voltage of the voltage application step (2a) and in the range of 6 to 14 V for 1 to 30 minutes, where the voltage is a direct-current pulse voltage with a frequency of 1 to 50 kHz having a ratio of a voltage applying period per cycle of 10 to 70%, and the area to be contacted by a skin in the iontophoresis is 1 to 50 cm$^2$ and the current density is maintained at 0.1 to 0.3 mA/cm$^2$.

20. An apparatus for iontophoresis which is provided with:

(i) an applicator comprising (ia) an electrode applicable with a direct-current voltage and (ib) an interface conductible to the electrode, capable of contacting a skin, possessing a calcitonin, its derivative having similar function or activity to the calcitonin or a salt thereof, transmittablly and capable of being supplied with a liquid for dissolving the calcitonin, its derivative or a salt thereof, (ii) an electric power supply for applying a direct-current voltage to the electrode, and (iii) a voltage stabilizing means for applying a substantially constant direct-current voltage in the range of 3 to 20 V supplied from the electric power supply to the electrode with maintaining a current density of 0.05 to 0.5 mA/cm$^2$.

21. A method of applying a voltage for enhancing transdermal absorption of a calcitonin with the use of an applicator comprising an electrode applicable with a direct-current voltage, and an interface conductible with the electrode, capable of contacting a skin, possessing a calcitonin, its derivative having similar function or activity to the calcitonin or a salt thereof transmittablly and capable of being supplied with a liquid for dissolving the calcitonin, its derivative or a salt thereof, wherein a substantially constant direct-current voltage in the range of 3 to 20 V is applied to the electrode with maintaining a current density at 0.05 to 0.5 mA/cm$^2$, and wherein said process comprises:

(1) at least one cycle comprising;

(1a) a precedent voltage application step of applying a substantially constant voltage for 1 to 30 minutes, and (1b) a succeeding voltage application step of applying a substantially constant voltage, which voltage is lower than the applied voltage of the precedent voltage application step (1a), for 15 to 100 minutes, or (2) at least one cycle comprising;

(2a) a voltage application step of applying a substantially constant voltage in the range of 4 to 15 V for 1 to 30 minutes, (2b) a step of interrupting the voltage application for 1 to 30 minutes, and (2c) a voltage application step of applying a substantially constant voltage, which voltage is substantially the same as the applied voltage of the voltage application step (2a) and in the range of 4 to 15 V, for 1 to 30 minutes, where the current density in the voltage application steps (2a) and (2c) is maintained at 0.08 to 0.3 mA/cm$^2$.

22. A transdermal drug delivery process according to claim 1, wherein the calcitonin derivative is a compound shown by the following formula (II)

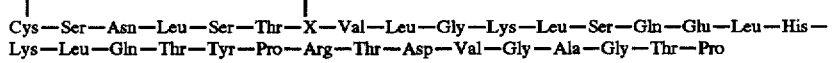

(II)

wherein X represents 2-aminosberic acid.

23. A transdermal drug delivery process according to claim 1, wherein the voltage application steps (1a) and (1b) are conducted continuously, or intermittently with an interval of 1 second to 60 minutes.

24. A transdermal drug delivery process according to claim 1, wherein the process comprises a plurality of cycles comprising;

(1a) a precedent voltage application step of applying a substantially constant voltage in the range of 5 to 15 V for 1 to 30 minutes, and (1b) a succeeding voltage application step of applying a substantially constant voltage, which voltage is lower than the applied voltage of the precedent voltage application step (1a) and in the range of 1 to 12 V, for 15 to 100 minutes.

25. An apparatus for iontophoresis according to claim 20, wherein the interface (ib) is treated with an adsorption-inhibitor.

26. An apparatus for iontophoresis according to claim 25, wherein the adsorption-inhibitor is a serum albumin or benzalkonium chloride.

* * * * *